(12) United States Patent
Steinbrenner et al.

(10) Patent No.: US 8,685,342 B2
(45) Date of Patent: Apr. 1, 2014

(54) DEVICE FOR RECEIVING AND DISPENSING LIQUIDS

(76) Inventors: Bernd Steinbrenner, Neckargemuend (DE); Roger Steinbrenner, Hirschhorn (DE)

( * ) Notice: Subject to any disclaimer, the term of this patent is extended or adjusted under 35 U.S.C. 154(b) by 960 days.

(21) Appl. No.: 12/801,552

(22) Filed: Jun. 15, 2010

(65) Prior Publication Data

US 2010/0252579 A1   Oct. 7, 2010

Related U.S. Application Data

(63) Continuation of application No. 11/578,826, filed as application No. PCT/EP2005/004694 on Apr. 30, 2005, now abandoned.

(30) Foreign Application Priority Data

May 10, 2004   (DE) .......................... 10 2004 023 517
May 13, 2004   (DE) .......................... 10 2004 023 690

(51) Int. Cl.
*B01L 3/02*   (2006.01)

(52) U.S. Cl.
USPC ........ 422/501; 422/516; 422/521; 73/863.32; 73/864; 73/864.01; 73/864.11; 73/864.13; 73/864.16; 73/864.18; 73/864.17

(58) Field of Classification Search
USPC ................ 422/501, 503–505, 516, 521, 923; 73/863.32, 864, 864.01, 864.11, 73/864.13, 864.16, 864.17, 864.18
See application file for complete search history.

(56) References Cited

U.S. PATENT DOCUMENTS

| | | | | |
|---|---|---|---|---|
| 3,498,342 A | * | 3/1970 | Sanderson | 141/238 |
| 3,855,868 A | * | 12/1974 | Sudvaniemi | 73/863.32 |
| 4,106,911 A | * | 8/1978 | Marcelli | 422/63 |
| 4,276,048 A | * | 6/1981 | Leaback | 436/180 |
| 4,498,510 A | * | 2/1985 | Minshew et al. | 141/27 |
| 4,511,534 A | * | 4/1985 | Bennett et al. | 422/501 |
| 4,626,509 A | * | 12/1986 | Lyman | 435/283.1 |
| 5,497,670 A | * | 3/1996 | Carl | 73/863.32 |
| 6,244,119 B1 | * | 6/2001 | Theran | 73/864.17 |
| 6,258,324 B1 | * | 7/2001 | Yiu | 422/526 |
| 6,374,683 B1 | * | 4/2002 | Hunicke-Smith et al. | 73/864.17 |

(Continued)

*Primary Examiner* — Brian R Gordon
(74) *Attorney, Agent, or Firm* — Paul Vincent

(57) ABSTRACT

A device for receiving and dispensing liquids has a plurality of piston-cylinder units (1, 1', 1") which are respectively arranged on a piston plate (2) and a cylinder plate (3). The liquid is received and dispensed by displacing the pistons (1') in the cylinders (1") by changing the distance between the plates (2, 3), perpendicularly to the plate planes, by means of a drive mechanism (6) and a plate guiding system. The volume can be determined by an upper abutment (4) and a lower abutment (5), at least one of said abutments being regulatable by a regulating means (8). The device is suitable for handling precise volumes of a larger number of piston-cylinder units (1, 1', 1") in a technically simple manner. To this end, the same receiving and dispensing volumes of the piston-cylinder units (1, 1', 1") are ensured with low requirements in terms of the surface parallelism of the plate planes during the movement in the plate guiding device, by structuring and arranging the abutments (4, 5) in such a way that the parallelism of the plates (2, 3) is obtained in the upper (9) and lower (10) abutment positions.

25 Claims, 3 Drawing Sheets

(56) References Cited

U.S. PATENT DOCUMENTS

| | | | |
|---|---|---|---|
| 6,582,664 B2 * | 6/2003 | Bevirt et al. | 422/501 |
| 6,805,840 B1 * | 10/2004 | Tajima | 422/501 |
| 6,869,571 B2 * | 3/2005 | Ingenhoven et al. | 422/510 |
| 6,989,131 B2 * | 1/2006 | Karlsson et al. | 422/528 |
| 7,125,727 B2 * | 10/2006 | Massaro | 436/180 |
| 7,185,551 B2 * | 3/2007 | Schwartz | 73/864.16 |
| 7,682,568 B2 * | 3/2010 | Jarvimaki et al. | 422/500 |
| 7,943,393 B2 * | 5/2011 | Gjerde et al. | 436/178 |
| 8,034,304 B2 * | 10/2011 | Karlsson et al. | 422/501 |
| 2004/0013572 A1 * | 1/2004 | Moore et al. | 422/99 |
| 2011/0318241 A1 * | 12/2011 | Danehy et al. | 422/500 |
| 2013/0068041 A1 * | 3/2013 | Naumann et al. | 73/864.01 |

* cited by examiner

DEVICE FOR RECEIVING AND DISPENSING LIQUIDS

This application is a continuation of Ser. No. 11/578,826 filed Oct. 19, 2006 now abandoned as the national stage of PCT/EP2005/004694 filed on Apr. 30, 2005 and claims Paris Convention priority of DE 10 2004 023 517.1 filed May 10, 2004 and DE 10 2004 023 690.9 filed May 13, 2004 the entire disclosures of which are hereby incorporated by reference.

BACKGROUND OF THE INVENTION

The invention concerns a device for receiving and dispensing liquids, with a plurality of piston-cylinder units which are disposed on a piston plate and a cylinder plate, respectively, wherein the liquid is received and dispensed by displacing the pistons in the cylinders by changing the distance between the plates using a drive mechanism and a plate guidance, perpendicularly to the plate planes, wherein the volume can be determined by an upper and a lower stop, at least one of which can be adjusted using at least one adjusting means.

In modern biological research, high-throughput methods are increasingly used, i.e. mass processing of samples, which are nearly always associated with pipetting steps. The samples are processed in plates having 96, 384 or even 1563 depressions in a standardized format. The large number of necessary pipetting steps can practically no longer be dealt with using conventional manual 8 or 12 channel pipettes. For this reason, pipetting automats having 96 or 384 channels are used (Beckman-Coulter, Gilson, Tecan, Zymark, Quiagen, Robbins, Zinsser, Perkin Elmer etc.). These devices are, however, extremely expensive, require a large amount of floor space and a large number of staff for programming, operating and maintenance. The piston unit of these automated pipetting systems is moved parallel upwards and downwards with extreme accuracy by rapidly rotating spindle drives. Stopping at a defined Z position exactly defines the pipetting volume.

A spindle drive of this type, having the required rapid and precise simultaneous spindle speed, is inappropriate for a pipetting system which is operated manually or with a simple drive, since either the mechanical devices or the control and drive are excessively complex or expensive.

U.S. Pat. No. 5,540,889 discloses a simple mechanical device having the features of the above-mentioned type. In this device, the piston plate is moved relative to the cylinder plate by a manual drive rod mounted to the center of the piston plate. An adjustable stop for presetting the pipetting volume is provided on the manual drive rod. The parallelism between the piston plate and the cylinder plate is thereby achieved by the manual drive rod guidance and optionally also by the piston guidance in the cylinders. This principle corresponds to the conventional multi-channel pipettes (the above-mentioned 8 or 12-channel pipettes). U.S. Pat. No. 5,540,889 defines the term "microvolume" as a volume on the order of a microliter in a range between about ½ microliter to 10 microliters. However, this mechanism of prior art is deficient with regard to handling such very precise volumes during pipetting, since these guidances cannot guarantee absolute parallelism and thereby exactly identical volumes of the liquid to be pipetted, compared to the controlled spindle drives of the above-mentioned automatic units, wherein excessive expense to ensure exact plate guidance would, in turn, be uneconomical. This problem increases with the number of piston-cylinder units and thereby with the size of the plates, such that these guidances can simultaneously operate either only a few piston-cylinder units or volume accuracy is not possible.

It is therefore the underlying purpose of the invention to modify a device of the above-mentioned type in such a manner that it is suitable for handling very precise volumes of a larger number of piston-cylinder units with little technical difficulty.

SUMMARY OF THE INVENTION

This object is achieved in accordance with the invention, while guaranteeing identical receiving and dispensing volumes of the piston-cylinder units with low demands with regard to surface parallelism of the plate planes during motion in the plate guidance, by designing and disposing the stops in such a manner that the stops ensure that the plates are parallel in the upper and lower stop positions.

In accordance with the invention, uniform motion of all pistons, i.e. permanent parallelism between piston and cylinder plates during the entire pipetting process, is not required in order to pipette exact volumes. To obtain accurate received or dispensed volumes it is sufficient that all piston-cylinder units are at the same position at only two times: at the lower and upper end positions. This is ensured by the stops. When these two positions, which correspond to the start and end of liquid reception or, vice versa, liquid dispensing, are exactly correct, it is irrelevant for the exactness of the volume whether the plates are exactly parallel inbetween, since any irregularity is compensated for at the latest when the respective stop is reached. This applies both for receiving and dispensing liquid. The precision therefore does not depend on the pipetting drive.

The invention thereby meets two conditions for precise and reproducible pipetting.

1. The path of the piston-cylinder units, and thereby the size of the very precise volumes can be exactly adjusted by the separation between the lower stop and the upper stop.

2. The plates are aligned exactly in parallel by the stops at the initial and end positions which are decisive for determining the volumes.

All piston-cylinder units have thereby moved through the same distance, which does not only exactly define the pipetting volume but also ensures that it is identical for each individual piston-cylinder unit of the system. Each unit pipettes the same volume, and all volumes can be simultaneously adjusted with high accuracy. Moreover, the operating forces are also within a practical range.

The above-presented device represents the first inexpensive device for performing a large number of parallel pipetting processes for high throughput work. No great investment is required, and the running costs and the overall weight of the device are substantially less compared to the above-mentioned automats. This is beneficial, in particular, for small companies, universities or institutes and companies in developing countries.

The inventive device closes the gap between multi-channel pipette and fully automated systems. It permits parallel reception or dispensing of many, preferably 96 liquid samples. The volume can be freely selected and exactly adjusted. The pipetting process itself is simple and easy to learn and corresponds largely to conventional manual pipetting which has been practiced for decades.

For manual operation, and also for motor drive, the up and down motion between the stops need not be controlled. An electronic control or electric drive is therefore not necessary, although a very simple means of this type could nevertheless be implemented. Once they have been set parallel to each other, the stops can be adjusted by a simple adjusting motion using a display means. The system can therefore be operated without extensive programming. Even unskilled staff can handle operation thereof without requiring time-consuming and expensive training. As in conventional, manual pipettes, faultless operation can be visually controlled at any time. The system can be quickly and flexibly adjusted to the respective requirements and can be used even when the space is limited, e.g. on sterile workbenches, due to its small dimensions.

The stops may be formed in different ways. They must only ensure that the plates, i.e. the piston plate and the cylinder plate, are parallel relative to each other in the upper and lower stop positions. When e.g. the piston plate is moved, the cylinder plate may be used as lower stop or bear such stops. In this case, only one upper stop must be mounted. This stop may also be a flat plate or consist of two linear stops. In a suitable fashion, each of the upper and lower stops has at least three stop points which abut the outer area of the moved plate. A minimum of three points is required to define the exact position of a surface. Pipetting processes are generally performed using working plates having an orthogonal grid and therefore a rectangular shape. For this reason, the piston plate and the cylinder plate will also have a rectangular shape. In this case, four stop points at the plate corners would be suitable, wherein, as mentioned above, three are also clearly possible.

The stops are preferably provided with means for adjusting the parallelism of the stop positions, which provides both exact initial setting and exact further readjustment.

In order to maximally facilitate adjustment of the volume, the invention proposes to design the adjusting means for adjusting the volume such that the stop points of the adjustable stop can simultaneously be adjusted in height. In this fashion, the volume can be adjusted through one single operation, wherein the parallelism of the plates in the end positions and thereby exact volumes of all piston-cylinder units are ensured, which may be achieved in different ways. The stop points may e.g. be adjusted by stepping motors. This can be realized with a very simple control means with one single display.

Another possibility is simultaneous adjustment of the stop points using a transmission. The stop points may e.g. be adjusted by threaded spindles or by adjustment nuts which can be screwed on rigid threaded spindles, which are simultaneously moved by an adjusting means via a toothed belt and toothed wheels. This adjustment can be performed without the plate abutting against and loading the stop. When the stop or the stop points are to be moved towards an abutting plate, e.g. the piston plate, the latter should suitably be previously moved away to ensure smooth running and reduce the required force. Clearly, measures may be taken to ensure this, such as blocking of the adjusting means or automatically moving away the plate when the adjusting means for the stop are initially actuated. In general, the user will be prompted automatically to move away the plate, since the adjusting means are blocked by the abutting plate or are difficult to access. The requirements in view of force and load resistance can therefore not be compared to the requirements for the spindle drives of the automatic devices. The adjustment of the stops or stop points of the inventive device, consequently requiring little force, while obtaining high accuracy with simple means. This adjusting means then suitably comprises a display means which displays the adjusted volumes.

It is essential for the volume adjustment design that the adjusting mechanism is released from all force-related loads, in particular, those of the drive required for the pipetting process, thereby obtaining high accuracy with little expense.

The device is advantageously used when a considerably higher number of piston-cylinder units are required than for a 8- or 12-channel pipette, which are designed in a grid-like arrangement, e.g. with 96 units. For this reason, disposing the device on a working plate having the same number of working positions is problematic. It is therefore proposed to dispose the piston plate, the cylinder plate, the stops and the drive in a pipetting head, which is suspended on a stand using a vertical guidance. It is also advantageous for the stand to have means for positioning the pipette head towards a working plate for pipetting in order to align the grid arrangement of the piston-cylinder units with the grid arrangement of the working positions on the working plate. This particularly accelerates working without excessively increasing the skill requirements.

Processing with several working plates is often necessary, e.g. to receive a liquid from a reservoir and dispense it to a working plate for processing. It is also feasible to repeatedly receive and dispense liquids to accelerate processing without having to repeatedly exchange the working plates. Liquid receptacles, e.g. pipette tips, must often be accommodated in a grid-like arrangement (see below). A liquid is subsequently received, which is then dispensed and the liquid receptacles are finally removed. This would require an arrangement of four working plates. Towards this end, further positioning means for working plates are provided, which can optionally be aligned with the grid arrangement of the piston-cylinder units.

There are different possibilities of providing several positioning means for working plates. One proposal consists in disposing the positioning means on a rotating disk to sequentially align several working plates in accordance with the grids. According to a further proposal, the stand has a horizontal guidance for the pipetting head and several positioning means for working plates disposed next to each other below the horizontal guidance, wherein positioning aids are provided for allocating the grids to the horizontal guidance. Another possibility is to provide several positioning means for working plates, which can be displaced to positions defined by positioning aids, using at least one horizontal guidance therefor, e.g. displaceable trays, such that the working plates located there can be associated with the grid of the piston-cylinder units. The last-mentioned possibility can also be combined with the above-mentioned by providing horizontal guidances for the working plates, which extend transversely to the horizontal guidance for the pipetting head. When the two above-mentioned embodiments are each limited to two positionings, the positioning aids may each be end stops of the horizontal guidances. In this case, the above-mentioned four, frequently required working plates can be positioned (see FIG. 2). Other positions may clearly also be designed by providing locking positions between the stops.

At least one lower stop is preferably provided for the vertical motion of the pipetting head. It adjusts a stop position for a vertical downward motion, in which the desired pipetting process can take place, since the correct height for receiving or dispensing liquid is predetermined relative to the respective working plates. For this reason, the at least one lower stop can suitably adjust the immersion depth into the liquid receptacles of the working plates. If e.g. several working plates are in positioning means below the horizontal guidance for the pipetting head, one stop may be provided for each positioning means, to adjust the correct height above the respective working plates.

In order to facilitate and accelerate operation, the vertical guidance of the pipetting head is associated with a weight balancing means, which is dimensioned to permit smooth vertical motion, requiring little force. This may be a counter weight. A spring is preferably used which does not excessively increase the overall weight of the device. A balance spring is thereby particularly suited, since it has nearly linear characteristics. For this reason, the force required for the vertical motion is constant along the entire motion path. For safety reasons, the vertical guidance of the pipetting head may have an associated lift stop or brake which reacts to excessive acceleration. This is suitable to prevent dropping and avoid accidents, which may happen e.g. should the spring break. A hydraulic or pneumatic lift stop or brake, e.g. a pneumatic spring could also be used.

In order to facilitate working, the drive mechanism for the piston-cylinder units can advantageously be operated by a manual lever with transmission. This may e.g. be a corresponding lever transmission or toothed wheel or toothed rack transmission or a combination of both. There are clearly further possibilities.

Since the cylinder plate should suitably be positioned at a certain height relative to the working plates to receive or dispense liquids, the moved plate advantageously is the piston plate, such that the drive is advantageously associated with the piston plate. In this case, the drive moves the piston plate into its lower stop position and restoring springs return it into the upper stop position. This particularly facilitates operation and prevents the piston plate from resting in an undefined position.

The pistons may be sealed with respect to the cylinders. This is advantageous, in that the piston and cylinders need not be accurately adjusted, with sealing being ensured, and a certain tolerance of parallelism of the plates during adjustment is possible without causing jamming. The seals may be designed as sealing rings disposed on the pistons. The cylinder plate may also be divided in a horizontal direction, with elastic sealing material being disposed therein, such that the cylinder diameters can be adjusted at the sealing locations through means for compressing the plate parts, wherein the pistons move in the area of the sealing locations. The sealing material may e.g. be a perforated plate of elastic material or each individual cylinder may have an associated annular elastic sealing element. This design is advantageous in that abutment between the seals and the pistons can be set and readjusted.

The cylinders may be directly provided with suction openings, or receiving means for disposing liquid receptacles, in particular pipette tips, on the lower end of the cylinder. For this reason, only the latter are wet by the liquid and the piston-cylinder units serve as suction devices which generate the underpressure required for suctioning, and blow out the liquid located in the liquid receptacles through downward motion. In this fashion, only the liquid receptacles must be exchanged after a working step or prior to exchange of the liquid to be pipetted. The liquid receptacles, i.e. tubes or pipette tips, may be provided with elastic rings to ensure safe fixing and proper seating, even when the liquid receptacles or pipette tips have inaccurate diameters.

A certain force is required to receive a large number of such liquid receptacles or pipette tips, e.g. the whole grid, at once. Force transmission is therefore proposed which presses the pipetting head for receiving the liquid receptacle, in particular the pipette tips, against a liquid receptacle support, in particular pipette tip support, located in a positioning means, or vice versa. The force transmission may e.g. be a translation lever which acts between the stand and pipetting head, forcing the latter towards the liquid receptacle support, in particular pipette tip support. Due to this force transmission, the pipetting drive need not be used for this purpose, and it need not be designed to withstand such high forces.

In another suitable fashion, a liquid receptacle or pipette tip wiper is provided, which may be a perforated plate operated by a lever, and disposed below the cylinder plate for vertical displacement. The holes must thereby be larger than the cylinder receiving means, but smaller than those of the liquid receptacles or pipette tips, to sweep them from the receiving means.

For handling these liquid receptacles, such as pipette tips, remaining liquid is advantageously blown out. Towards this end, the lower stop is designed as a latch which defines the lift which is decisive to determine the volumes, by parallel orientation of the plate. The plate can then be moved further by overcoming the retention force or disengaging the latch, to blow out any residual liquid.

In a further development of the invention, the received liquid can be dosed by disposing at least one latch-like intermediate stop between the upper and lower stops which also aligns the plates in parallel and can be overcome with increased force or through release. One or more of such intermediate stops have the purpose that the volumes of liquid defined after one single liquid reception are subsequently dispensed to two or more working plates. This simplifies processing in that several working plates are provided with the same liquid. This at least one latch-like intermediate stop should clearly also be adjustable such that the volumes can also be exactly determined relative to the sequentially dispensed liquid.

The invention is explained below with reference to an embodiment shown in the drawing.

DESCRIPTION OF THE PREFERRED EMBODIMENT

Figure 1:
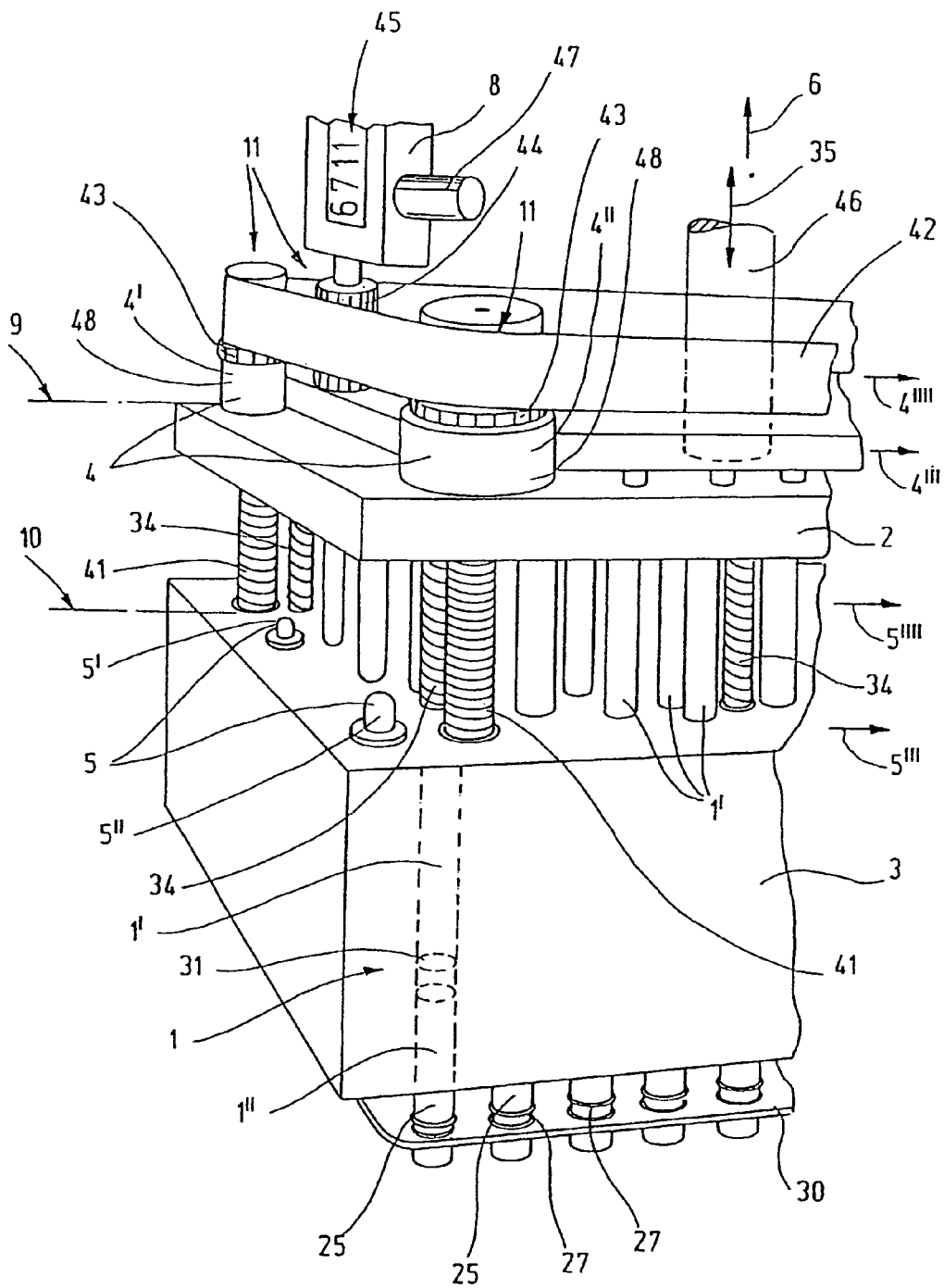
FIG. 1 shows the functional structure of the inventive device.

FIG. 1 shows the functional structure of an embodiment of the inventive device. Piston-cylinder units 1 are arranged like a grid, such that the piston 1' is located on a piston plate 2 and the cylinder 1" on a cylinder plate 3. The cylinders 1" of the embodiment shown are formed by providing the cylinder plate 3 with corresponding bores. In this fashion, a suction motion is generated by an upward motion of the piston plate 2 and a discharge motion is generated by a downward motion of the piston plate 2. In order to seal the pistons 1' tightly with respect to the cylinders 1", each of them may be provided with a sealing ring 31. In the illustration, a piston-cylinder unit 1 with piston 1', sealing ring 31 and cylinder 1" is shown in dashed lines as an example. In fact, a plurality of such units 1 are provided in a grid-shaped arrangement. In correspondence with conventional working plates 16, a grid of 96 piston-cylinder units 1 may be selected to handle the working positions on these working plates 16. Clearly, other grids may also be provided.

An adjusting motion 35 of a drive 6, of which only the drive rod 46 is shown, moves the piston plate 2 to a lower stop position 10. In this position, the piston-cylinder units 1 are ready for suctioning a liquid. The drive 6 must now only be deactivated or the locking (not shown) must be released to permit an upward return motion of the piston plate 2 by the restoring springs 34 to an upper stop position 9. The motion path can be predetermined through corresponding measures such that it can be repeated. In this position 9, a liquid is suctioned in. When the piston plate 2 is moved again in a downward direction, the liquid is once more discharged.

In accordance with the invention, exact positioning of the piston plate 2 relative to the cylinder plate 3 in the upper stop position 9 and the lower stop position 10 ensures that the volumes which are suctioned and dispensed by all piston-cylinder units 1 are exactly the same. An upper stop 4 and a lower stop 5 ensure this. In order to obtain maximally exact positioning of the piston plate 2, the stops 4 and 5 each consist of stop points 4', 4", 4''' and 4'''' or stop points 5', 5", 5''', and 5'''' which abut the outer areas of the piston plate 2, thereby providing good parallel alignment thereof. (Since the illustration is broken away, the correspondingly arranged stop points 4''' and 4'''', 5''', 5'''' are not shown: the arrows indicate their position). The lower stop points 5', 5", 5''', and 5'''' can only be adjusted to obtain exact parallel alignment of the piston plate 2 in the lower support position 10. These stop points 5', 5", 5''', and 5'''' may also be designed to form the stop 5 in the illustrated stop position 10 but may be urged downwards under an increased force to provide the above-mentioned additional blow-out function, i.e. to remove residual adhering liquid.

In contrast thereto, the upper stop points 4', 4", 4''' and 4'''' can be set and simultaneously also adjusted to set the volumes to be received and dispensed. This is effected by a transmission 11 which simultaneously adjusts the stops relative to the stop points 4', 4", 4''' and 4''''. This transmission 11 consists of one adjusting means 8 comprising an adjusting wheel 47, which can drive a drive wheel 44. In correspondence with rotation on the adjustment wheel 47, the adjusted volume is displayed on the volume display 45. The drive wheel 44 drives a toothed belt 42 via the adjustment wheel 47, the toothed belt 42, in turn, simultaneously driving drive gears 43. These drive wheels 43 are connected to adjustment nuts 48 which are disposed on the threaded spindles 41, such that their heights are simultaneously adjusted. These adjustment nuts 48 form stop points 4', 4", 4''' and 4'''' at their lower ends, such that all adjustment points 4', 4", 4''' and 4'''' can be simultaneously adjusted in this fashion, each adjustment ensuring an upper stop position 9 with exactly parallel surfaces to the piston plate 2 relative to the cylinder plate 3. The drive wheel 44 may alternatively also be a drive gear 43.

In order to prevent soiling of the piston-cylinder units 1, these only suction and discharge air, and the liquid does not reach the cylinders 1". Towards this end, receiving means 25 are provided at the lower end of the cylinders 1" onto which the liquid receptacles can be disposed, which are preferably pipette tips 26. The illustrated unit is moved exactly over a pipette tip support 28 for receiving such pipette tips 26. When the unit is moved downwards, the receiving means 25 accept the pipette tips 26 contained in the pipette tip support 28. When other liquid receptacles are used, the process is correspondingly adapted. In order to ensure safe retention on the receiving means 25, elastic rings 27 are disposed which compensate for even small dimensional differences to always ensure the required retention force.

A liquid receptacle or pipette tip wiper 30 is moreover shown which is designed as a perforated plate and is illustrated in a position below the elastic rings 27, i.e. pipette tips 26 have been ejected. For receiving the pipette tips 26, the pipette tip wiper 30 is moved in an upward direction e.g. until it abuts the cylinder plate 3. The pipette tips 26 can then be disposed on the receptacles 25 and are retained at the elastic rings 27 since they have a slightly smaller diameter than the latter. When the pipette tip wiper 30 is moved again into the illustrated position, the pipette tips 26 are swept off and fall e.g. into a support provided for this purpose. The holes of the perforated plate must be larger than the receiving means 25, including the elastic rings 27, but smaller than the diameters of the pipette tips 26 to perform this removal function.

Figure 2:
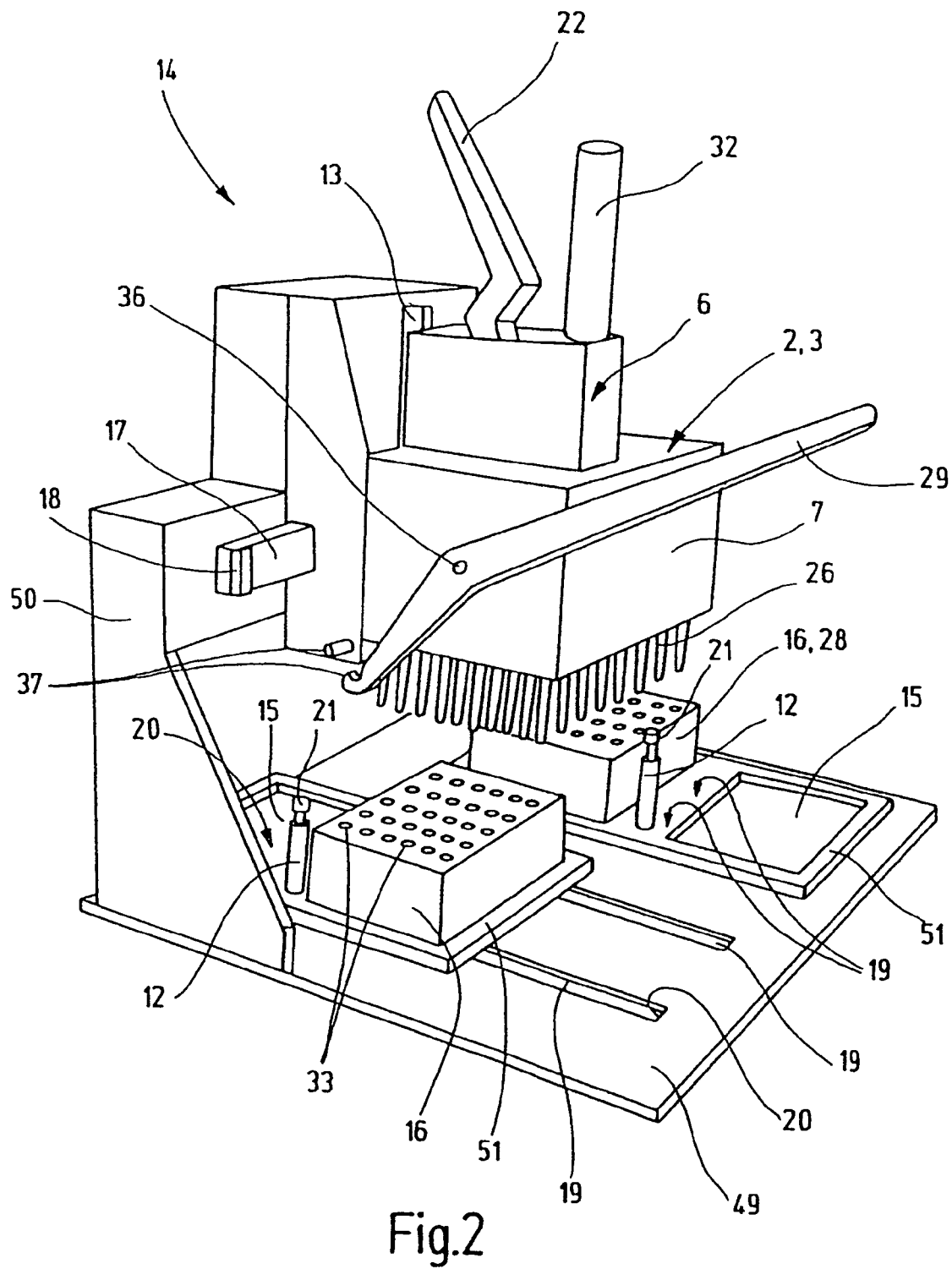
FIG. 2 shows the arrangement of the inventive device on a stand using a pipetting head.

FIG. 2 shows the arrangement of the device shown in FIG. 1 on a stand 14. The device of FIG. 1 is in a pipetting head 7, wherein a drive mechanism 6 for the pipetting process is disposed above the pipetting head 7, which can be operated using a pivotable hand lever 22 and a fixed retaining handle 32. The stand 14 consists of a base plate 49 and a structure 50 on which the pipetting head 7 is disposed using a vertical guidance 13. The pipetting head 7 can be displaced in this vertical guidance 13 such that liquid receptacles such as pipetting tips 26 can be received by a liquid receptacle or pipette tip support 28 such that liquid is also suctioned into the pipette tips 26, wherein this liquid can, in turn, be dispensed to another working plate 16, having working positions 33, e.g. depressions into which the liquid is disposed. In order to obtain correct positioning in height for these processes, lower stops 12 are provided for the pipetting head 7, which can be adjusted using adjustment screws 21 in correspondence with the respective requirements. The stops 12 are associated with working plates which can be positioned in correspondence with the positioning means 15, and can be adjusted thereto.

A horizontal guidance 17 for the pipetting head 7 is moreover provided to displace it between the two illustrated working plates 16 which are positioned using the positioning means 15. To align the grids, both ends of the horizontal guidance 17 have positioning aids 18 which are designed as stops.

In order to be able to operate using even more working plates 16, two displaceable trays 51 are disposed on the base plate 49 using horizontal guidances 19 which each contain two positioning means 15 for working plates 16. These positioning means 15 may e.g. be depressions into which the working plates 16 exactly fit. The trays 51 can be respectively displaced on the horizontal guidances 19 between two stops 20 which are located at the ends of these horizontal guidances 19 such that each end position produces precise grid conformity between a working plate 16 in the positioning means 15 and the pipetting head 7. Adjustable positioning means 15 for positioning working plates 16 of different sizes are of course also possible. The plates 2, 3 or the pipetting head 7 may be exchangeable and the positioning aids 18, 20 may be adjustable for different grids.

Accepting pipetting tips 26 or other liquid receptacles on the receiving means 25 requires an increased force, in particular, when numerous pipette tips, e.g. a grid of 96 tips are to be received. For this reason, a transmission lever 29 is provided. This transmission lever 29 is pivotably disposed on the pipetting head 7 via a hinge 36 and has a support 37 into which the end of the transmission lever 29 engages to force the pipetting head 7 with increased force in a downward direction such that the receiving means 25 engage and capture the entire grid of pipetting tips 26. The transmission lever 29, one side of which is shown, may clearly also be disposed on both sides of the pipetting head 7, wherein a transverse bar at the ends provides common actuation.

Figure 3:
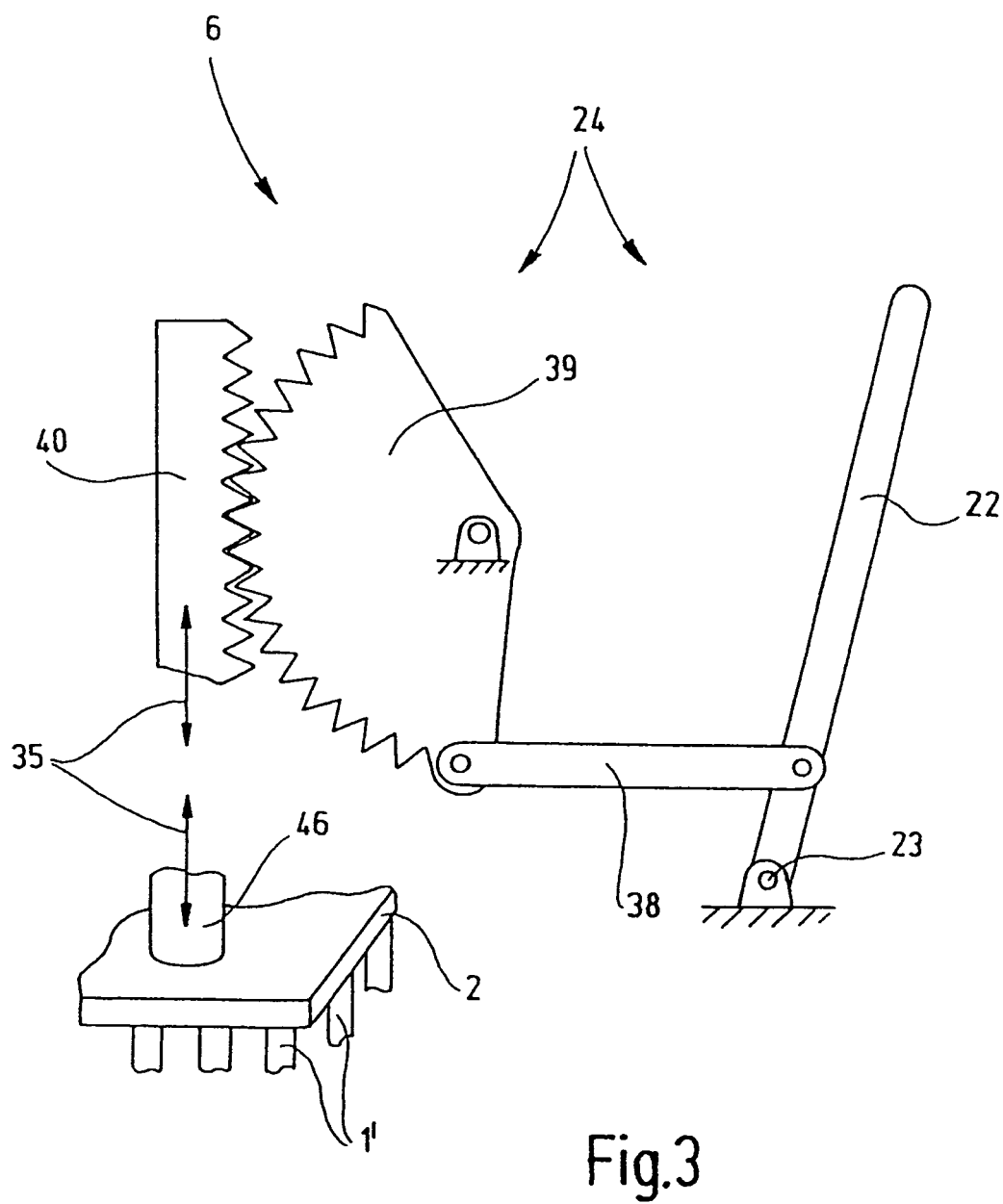
FIG. 3 shows a possible drive mechanism for the pipetting process.

FIG. 3 shows one variant of a drive mechanism 6 for the pipetting process. The hand lever 22 is thereby hinged to the pipetting head 7 via a hinge 23, and transmits the pivot motion to a toothed wheel 39, which may also be designed as toothed wheel segment, via a transmission rod 38. It engages in a toothed rack 40 which is connected to the drive rod 46 (shown in FIG. 1). The double arrow 35 indicates the adjusting motion to the piston plate 2. This obtains corresponding transmission 24 between the hand lever 22 and the adjusting motion 35 of the piston plate 2.

The illustration clearly shows only one feasible embodiment of the invention. It could have a simpler construction e.g. in the form of a device as shown in FIG. 1 which can be moved above a working plate 16 without stand 14 using a corresponding structure. It would also be possible to adjust the stop 4 or the stop 5 by stepping motors or provide a simple motor drive instead of the hand lever actuation. The cylinder plate 3 could, of course, also be moved instead of the piston plates 2. In this case, a working plate 16 to be operated would have to be moved as well to maintain the correct working distance. In a further design, intermediate stops could be provided between the stops 4 and 5, which lock like latches and ensure that the received liquid can be dispensed sequentially in several portions. Further modifications are feasible.

LIST OF REFERENCE NUMERALS 1 piston-cylinder unit
1' piston
1" cylinder
2 piston plate
3 cylinder plate
4 upper stop (can be set and adjusted)
4', 4", 4''', 4'''' stop points of the upper stop
5 lower stop (can be set)
5', 5", 5''', 5'''' stop points of the lower stop
6 drive mechanism for pipetting process
7 pipetting head
8 adjusting means for stop
9 upper stop position
10 lower stop position
11 transmission for simultaneous stop adjustment
12 lower stop for pipetting head
13 vertical guidance of the pipetting head
14 stand
15 positioning means for working plates
16 working plates
17 horizontal guidance of the pipetting head
18 positioning aids for pipetting head (e.g. stops)
19 horizontal guidance for positioning means for working plates
20 positioning aids for positioning means (e.g. stops)
21 adjusting screw
22 hand lever
23 hinge of hand lever
24 transmission
25 receiving means
26 pipette tips
27 elastic rings
28 liquid receptacles or pipette tip supports
29 transmission lever
30 liquid receptacle or pipette tip wiper
31 sealing ring
32 retaining handle
33 working positions on the working plates
34 restoring springs
35 adjustment motion for pipetting
36 hinge of the transmission lever on the pipetting head
37 support of the transmission lever on the stand
38 transmission rod
39 toothed wheel or toothed segment
40 toothed rack
41 threaded spindles
42 toothed belt
43 drive gear
44 drive wheel
45 volume display
46 drive rod
47 adjusting wheel
48 adjustment nuts
49 base plate
50 structure
51 tray

We claim:

1. A device for receiving and dispensing liquids to and from liquid receptacles or pipette tips, the device comprising:
a piston plate having a plurality of pistons;
a cylinder plate defining a plurality of cylinders, wherein each piston engages one cylinder;
a drive mechanism connected to at least one of said piston plate and said cylinder plate, said drive mechanism disposed, structured and dimensioned to change a separation between said piston plate and said cylinder plate, thereby displacing said pistons in said cylinders to receive and dispense the liquids;
a plate guidance to direct relative motion between said piston plate and said cylinder plate;
at least three upper stops, said upper stops disposed in and defining an upper stop plane; and
at least three lower stops, said lower stops disposed in and defining a lower stop plane, said lower stop plane being parallel to said upper stop plane, with equal dosed liquid volumes for all pistons and cylinders being defined by displacement of said piston plate relative to said cylinder plate from said upper stop plane to said lower stop plane, wherein said plate guidance directs said relative motion between said piston plate and said cylinder plate in a direction substantially perpendicular to said upper and said lower stop planes.

2. The device of claim 1, further comprising a liquid volume adjusting mechanism connected to at least one of said upper stops and said lower stops to cause said piston plate and said cylinder plate to assume a mutually parallel configuration defined by said lower stops and said upper stops.

3. The device of claim 2, where said liquid volume adjusting mechanism is structured to adjust a parallelism of said upper and lower stops.

4. The device of claim 2, wherein said liquid volume adjusting mechanism is structured to simultaneously adjust a height of said upper stops or of said lower stops.

5. The device of claim 4, wherein said liquid volume adjusting mechanism comprises stepping motors for adjusting said upper or said lower stops.

6. The device of claim 4, wherein said liquid volume adjusting mechanism comprises a transmission for simultaneously adjusting said upper or said lower stops.

7. The device of claim 1, further comprising a pipetting head and a stand having a vertical guidance, wherein said pipetting head is supported on said stand via said vertical guidance, said piston plate, said cylinder plate, said upper stops and said lower stops being disposed in said pipetting head.

8. The device of claim 7, wherein said pistons and said cylinders are disposed in a first grid arrangement and further comprising a working plate defining a second grid arrangement of positions, wherein said stand comprises at least one working plate positioning mechanism cooperating with said working plate to align said first grid arrangement of said pistons and cylinders with said second grid arrangement of positions on said working plate.

9. The device of claim 8, wherein said working plate positioning mechanism is connected to said working plate to align said working plate with said first grid arrangement of said pistons and said cylinders.

10. The device of claim 9, wherein said stand comprises a pipetting head horizontal guidance having positioning aids for grid alignment, wherein at least two said working plate positioning mechanisms are disposed below said pipetting head horizontal guidance.

11. The device of claim 10, wherein said at least two working plate positioning mechanisms are structured for displacement using at least one working plate horizontal guidance to assume positions defined by working plate positioning aids, thereby aligning said working plate with said first grid arrangement of said pistons and said cylinders.

12. The device of claim 8, further comprising at least one pipetting head lower stop, said pipetting head lower stop limiting a vertical motion of said pipetting head.

13. The device of claim 12, wherein said working plate has liquid receptacles, said at least one pipetting head lower stop adjusting an immersion depth into said liquid receptacles.

14. The device of claim 12, wherein said pipetting head lower stop is disposed on said working plate positioning mechanism.

15. The device of claim 1, wherein said drive mechanism comprises a hand lever and a transmission.

16. The device of claim 15, wherein said drive mechanism acts on said piston plate.

17. The device of claim 16, wherein said drive mechanism moves said piston plate into said lower stop plane and further comprising restoring springs for returning said piston plate to said upper stop plane.

18. The device of claim 1, further comprising seals, said seals disposed between and sealing said pistons with respect to said cylinders.

19. The device of claim 18, wherein said cylinder plate is divided in a horizontal direction into a first and a second part, wherein an elastic sealing material is disposed between said first and said second parts, and further comprising a compressing mechanism for urging said first part towards said second part, wherein said elastic sealing material is disposed, structured and dimensioned in such a fashion that said compressing mechanism adjusts cylinder diameters at sealing locations at which said pistons move.

20. The device of claim 8, wherein lower ends of said cylinders have receiving elements structured to hold the liquid receptacles or pipette tips.

21. The device of claim 20, wherein said receiving elements have elastic rings.

22. The device of claim 20, wherein said pipetting head has a force transmitter effecting relative pressing movement between said pipetting head and the liquid receptacles or pipette tips for accepting the liquid receptacles or pipette tips in said receiving elements, wherein the liquid receptacles or pipette tips are disposed in said working plate.

23. The device of claim 22, wherein said force transmitter comprises a transmission lever which acts between said stand and said pipetting head to urge said pipetting head towards said working plate.

24. The device of claim 20, further comprising a wiper for wiping-off the liquid receptacles or pipette tips, said wiper having a perforated plate disposed below said cylinder plate and comprising a lever for vertical displacement of the perforated plate, said plate having holes which are larger than said receiving elements.

25. The device of claim 1, wherein said lower stops are designed as a latch, at least one of said piston plate and said cylinder plate being further moved by overcoming a retention force or by disengaging said latch, thereby blowing out any residual liquid.

* * * * *